US009675283B2

(12) United States Patent
Lam (10) Patent No.: US 9,675,283 B2
(45) Date of Patent: Jun. 13, 2017

(54) METHODS FOR CLASSIFYING PLEURAL FLUID (71) Applicant: The University of Hong Kong

(72) Inventor: Ching-Wan Lam, Kowloon (HK)

(73) Assignee: The University of Hong Kong, Hong Kong (HK)

( * ) Notice: Subject to any disclaimer, the term of this patent is extended or adjusted under 35 U.S.C. 154(b) by 320 days.

(21) Appl. No.: 14/334,781

(22) Filed: Jul. 18, 2014

(65) Prior Publication Data
US 2015/0025339 A1    Jan. 22, 2015

Related U.S. Application Data (60) Provisional application No. 61/847,610, filed on Jul. 18, 2013.

(51) Int. Cl.
| | |
|---|---|
| G01N 33/92 | (2006.01) |
| A61B 5/145 | (2006.01) |
| A61B 5/1455 | (2006.01) |
| A61B 5/00 | (2006.01) |
| C12Q 1/32 | (2006.01) |
| G01R 33/44 | (2006.01) |
| A61B 5/055 | (2006.01) |
| A61B 5/08 | (2006.01) |
| G01R 33/465 | (2006.01) |

(52) U.S. Cl.
CPC .......... *A61B 5/14507* (2013.01); *A61B 5/055* (2013.01); *A61B 5/08* (2013.01); *A61B 5/1455* (2013.01); *A61B 5/4839* (2013.01); *C12Q 1/32* (2013.01); *G01N 33/92* (2013.01); *G01R 33/44* (2013.01); *G01R 33/465* (2013.01); *A61B 5/14532* (2013.01); *A61B 5/14539* (2013.01); *A61B 5/14546* (2013.01)

(58) Field of Classification Search
CPC ..................................................... G01N 33/92
USPC ..................................................... 436/71, 173
See application file for complete search history.

(56) References Cited

U.S. PATENT DOCUMENTS

| | | | | |
|---|---|---|---|---|
| 4,324,686 A * | 4/1982 | Mundschenk | ..... | G01N 15/1209 435/2 |
| 4,933,844 A * | 6/1990 | Otvos | .................. | G01R 33/465 128/922 |
| 5,343,389 A * | 8/1994 | Otvos | ..................... | G01N 33/92 436/173 |
| 6,194,222 B1 * | 2/2001 | Buechler | ................. | G01N 33/53 422/560 |
| 6,813,375 B2 * | 11/2004 | Armato, III | .......... | G06T 7/0012 382/131 |
| 2003/0119194 A1 * | 6/2003 | Otvos | ..................... | G01N 33/92 436/71 |
| 2005/0037510 A1 * | 2/2005 | Sharrock | ............... | G01N 21/274 436/164 |
| 2005/0181460 A1 * | 8/2005 | Ohno | ...................... | C07K 16/18 435/7.2 |
| 2006/0239909 A1 * | 10/2006 | Anderson | ............... | A61K 31/35 424/1.49 |
| 2007/0026424 A1 * | 2/2007 | Powell | .................. | C12Q 1/6886 435/6.14 |
| 2008/0187200 A1 * | 8/2008 | Degani | .................. | G06T 7/0016 382/131 |
| 2009/0028405 A1 * | 1/2009 | Degani | ................... | A61B 6/481 382/131 |
| 2009/0175783 A1 * | 7/2009 | Zubeldia | ............... | A61K 51/088 424/1.11 |
| 2010/0028876 A1 * | 2/2010 | Gordon | ............ | G01N 33/57423 435/6.11 |
| 2011/0010099 A1 * | 1/2011 | Adourian | ................. | G06F 19/12 702/19 |
| 2012/0021531 A1 * | 1/2012 | Ellis | .................... | G01N 21/8483 436/501 |
| 2013/0273573 A1 * | 10/2013 | Allauzen | ............ | G01N 33/6896 435/7.92 |
| 2014/0227715 A1 * | 8/2014 | Todd | ................... | G01N 33/6893 435/7.4 |
| 2014/0303041 A1 * | 10/2014 | Hayes | .................... | C07K 16/18 506/18 |
| 2015/0198583 A1 * | 7/2015 | Batra | ............... | G01N 33/56966 514/789 |

OTHER PUBLICATIONS

Hamm, H. et al, Chest 1987, 92, 296-302.*
Davis, S. D.et al, Journal of Computer Assisted Tomography 1990, 14, 192-198.*
Pfalzer B. The Journal of Laboratory and Clinical Medicine 1992, 120, 483-493.*
Metintas, M. et al, Clinica Chimica Acta 1997, 264, 149-162.*
Vaz, M. A. C. et al, Chest 2001, 119, 204-210.*
Light, R. W., New England Journal of Medicine 2002, 346, 1971-1977.*
Guleria, R. et al, Nationsl Medical Journal of India 2003, 16, 64-69.*
Baysal, T. et al, European Radiology 2004, 14, 890-896.*

(Continued)

*Primary Examiner* — Arlen Soderquist
(74) *Attorney, Agent, or Firm* — Pabst Patent Group LLP (57) ABSTRACT

Methods of classifying pleural fluid are disclosed. The methods typically include determining the level of indicator nanoparticles, such as lipids, particularly large lipids, in the pleural fluid of a subject. The level of lipids can be determined by nuclear magnetic resonance (NMR), such as proton NMR ($^1$H-NMR) by measuring the NMR signal corresponding to methyl protons, methylene protons, methene protons, or combinations thereof. The level of large lipids in pleural fluid can be carried out in vitro on a sample of pleural fluid obtained from the subject or in vivo using magnetic resonance spectroscopy (MRS). The pleural fluid can be classified as exudate or transudate with a sensitivity, selectivity, or combination thereof of 85%, 90%, 95%, 99%, or higher, a selectivity of 85%, 90%, 95%, 99%. The method can be coupled with diagnosing and/or treating the subject with a disease, disorder, or condition.

30 Claims, 4 Drawing Sheets

(56) References Cited

OTHER PUBLICATIONS

Kokturk, O. et al, Tüberküloz ve Toraks Dergisi 2005, 53, 33-38.*
Mulder, W. J. M. et al, Accounts of Chemical Research 2009, 42, 904-914.*
Hill, M. L. et al, Academic Radiology 2010, 17, 1359-1365.*
Ghosh, S. et al, Malaria Journal 2011, 10:330.*
Hamal. A. B. et al, Pulmonary Medicine 2013, Article ID 135036, 4 pages.*
Razi, E. et al, Tanaffos 2008, 7, 37-43.*
Chan, et al., "Quantitative analysis of pleural fluid cell-free DNA as a tool for the classification of pleural effusions", Clin Chem., 49(5):740-5 (2003).
Chen, et al, "Diagnostic value of pleural fluid adenosine deaminase activity in tuberculous pleurisy", Clin Chim Acta., 341(1-2):101-7 (2004).
Chen and Lam, "Protein zone electrophoresis of pleural effusion: the diagnostic separation of transudates and exudates", Clin Chem., 45(10):1882-5 (1999).
Cheung, et al., "In vivo lipid profiling using proton magnetic resonance spectroscopy in an experimental liver fibrosis model", Acad. Radiol., 18:377-83 (2011).
Cormode, et al., "Nanoparticle contrast agents for computed tomography: a focus on micelles", Contrast Media Mol. Imaging, 9:37-52 (2014).
Fawcett, "An introduction to ROC analysis", Pattern Recogn., 27:861-74 (2006).
Glunde, et al., "MRS and MRSI guidance in molecular medicine: targeting and monitoring of choline and glucose metabolism in cancer" ,NMR Biomed., 24(6): 673-90 (2011).
Jansen, et al., "1H MR spectroscopy of the brain: absolute quantification of metabolites", Radiology, 240:318-32 (2006).
Light, et al., "Pleural effusions: the diagnostic separation of transudates and exudates", Ann Intern Med., 77(4):507-13 (1972).
Otvos, et al., "Development of a proton nuclear magnetic resonance spectroscopic method for determining plasma lipoprotein concentrations and subspecies distributions from a single, rapid measurement", Clin. Chem., 38(9):1632-8 (1992).
Otvos, et al., "Quantification of plasma lipoproteins by proton nuclear magnetic resonance spectroscopy", Clin. Chem., 37(3):377-86 (1991).
Petersen, et al., "Quantification of lipoprotein subclasses by proton nuclear magnetic resonance-based partial least-squares regression models", Clin.Chem., 51(8): 1457-61 (2005).
Porcel, et al., "Diagnostic approach to pleural effusion in adults", Am. Fam. Physician, 1;73(7):1211-20 (2006).
Porcel, et al., "Pleural fluid C-reactive protein contributes to the diagnosis and assessment of severity of parapneumonic effusions", Eur. J. Intern. Med., 23 (5):447-50 (2012).
Porcel, "Pearls and myths in pleural fluid analysis", Respirology, 16(1):44-52 (2011).
Romero-Candeira, et al., "Is it meaningful to use biochemical parameters to discriminate between transudative and exudative pleural effusions", Chest, 122 (5):1524-9 (2002).
Stoyanova and Brown, "NMR spectral quantitation by principal component analysis", NMR, 14:271-7 (2001).
Valdes, et al, "Usefulness of triglyceride levels in pleural fluid", Lung, 188 (6):483-9 (2010a).
Valdes, et al., "Cholesterol in pleural exudates depends mainly on increased capillary permeability", Transl. Res., 155(4):178-84 (2010b).
Valdes, et al., "Diagnostic value of N-terminal pro-brain natriuretic peptide in pleural effusions of cardiac origin", Arch Bronconeumol., 47(5):246-51 (2011).
Vaz, et al., "Cholesterol in the separation of transudates and exudates", Curr. Opin. Pulm. Med., 7(4):183-6 (2001).
Wishart, et al., "HMDB 3.0 The Human Metabolome Database in 2013", Nucleic Acids Res., 41(Database issue): D801-807 (2013).
Worley, et al., "Utilities for quantifying separation in PCA/PLS-DA scores plots", Anal Biochem., 433:102-4 (2013).

* cited by examiner

METHODS FOR CLASSIFYING PLEURAL FLUID

CROSS-REFERENCE TO RELATED APPLICATIONS

This application claims benefit of U.S. Provisional Application No. 61/847,610, filed Jul. 18, 2013. Application No. 61/847,610, filed Jul. 18, 2013, is hereby incorporated herein by reference in its entirety.

FIELD OF THE INVENTION

The invention generally relates to methods of classifying a sample of pleural fluid as a transudate or an exudate and uses of the methods to assist in disease diagnoses.

BACKGROUND OF THE INVENTION

Pleural fluid (PF) is a thin layer of fluid in the pleural cavity which serves as an important physiological lubricant and mechanical barrier. The volume and flow of PF are tightly regulated. In disease states, the dynamic of PF flow is compromised, resulting in abnormal accumulation of PF. This condition is called pleural effusion.

In clinical practice, the first step in investigating the etiology of pleural effusion is typically to classify PF as exudative (high protein) or transudative (low protein). This classification is used to narrow down the differential diagnosis (i.e., etiology) of the underlying causes. For example, causes for exudative pleural effusion include lung cancer (primary or secondary), infections (pulmonary tuberculosis, non-tuberculosis pneumonia or empyema) and autoimmune disease, while causes for transudative pleural effusion include congestive heart failure, chronic kidney disease and liver cirrhosis.

PF can be classified into exudate and transudate according to Light's criteria (Light, et al., *Ann Intern Med.,* 77(4):507-513 (1972)). Briefly, Light, et al., performed a prospective study involving 150 pleural fluid samples, 47 transudates and 103 exudates and concluded that the presence of any one of the following features is highly suggestive of exudative pleural effusion: (1) the ratio of pleural fluid protein to serum protein is greater than 0.5; (2) a pleural fluid LDH is greater than 200 IU; or (3) the ratio of pleural fluid LDH to serum LDH is greater than 0.6. This set of criteria had been applied clinically for more than 40 years.

However, Porcel summarized the diagnostic accuracy of Light's criteria from 2115 subjects and reported a sensitivity ranged from 96.7% to 98.2% and specificity ranged from 69.4 to 77.7% (Porcel, *Respirology,* 16(1):44-52 (2011)). Other prospective studies have reported an even lower diagnostic specificity of 65-86%. The non-specificity of Light's criteria can cause misclassifications of PF. For example, transudative PF can be misdiagnosed as exudative PF, resulting in unnecessary testing and treatment of the subject. In a study involving 249 patients, classification of transudates based on clinical presentation could generate a misclassification rate of 42-44% (Romero-Candeira, et al., *Chest,* 122(5):1524-9 (2002)).

To enhance the diagnostic accuracy of PF classification, other biochemical markers/methods were considered in the laboratory evaluation of PF. For example, albumin gradient, NT-pro-BNP, BNP (Valdes, et al., *Arch Bronconeumol.,* 47(5):246-51 (2011)), C-reactive protein (CRP) (Porcel, et al., *Eur. J. Intern. Med.,* 23(5):447-50 (2012)), cell counts (both red blood cells and white blood cells), glucose concentration, pH value, adenosine deaminase (ADA) activity (Chen, et al, *Clin. Chim. Acta.,* 341(1-2):101-7 (2004), amylase, cholesterol (Vaz, et al., *Curr. Opin. Pulm. Med.,* 7(4):183-6 (2001), Valdes, et al., *Transl. Res.,* 155(4):178-84)), triglyceride (Valdes, et al, *Lung,* 188(6):483-9 (2010)), cell-free DNA (Chan, et al., *Clin Chem.,* 49(5):740-5 (2003)), protein zone electrophoresis (Chen and Lam, *Clin Chem.,* 45(10):1882-5 (1999)) among others. However, none of these tests can achieve both a sensitivity and specificity greater than 90%. Currently, there is no single marker that has both satisfactory sensitivity and specificity. Most of the markers have high sensitivity at the sacrifice of its specificity or vice versa.

Therefore, it is an object of the invention to provide methods for classifying pleural fluid as a transudate or an exudate with both high sensitivity and specificity.

It is a further object of the invention to provide methods of diagnosis and treatment including classification of pleural fluid as a transudate or an exudate with both high sensitivity and specificity.

SUMMARY OF THE INVENTION

Methods of classifying pleural fluid are disclosed. The methods typically include determining the level of indicator nanoparticles, particularly contrast agents or lipids, in the pleural fluid of a subject. For example, the method can include determining the level of lipids, particularly large lipids, in the pleural fluid of a subject.

Pleural fluid with a higher level of large particle lipids compared to a control is typically determined be exudate; whereas, pleural fluid with a lower level of large particle lipids compared to the control is typically determined to be transudate. The control can be an average threshold value determined by averaging the level of large particle lipids from known exudates and transudates. The threshold value can be determined using the same method of determining the level of large lipids as is used to determine the level of large lipids in the pleural fluid. Similarly, pleural fluid with a higher level of indicator nanoparticles compared to a control is typically determined be exudate; whereas, pleural fluid with a lower level of indicator nanoparticles compared to the control is typically determined to be transudate.

The level of indicator nanoparticles, such as contrast agents and large lipids, in pleural fluid can be compared to standard values indicative of exudate or transudate. For example, if the level of large particle lipids in the pleural fluid is within 5%, 10%, 15%, 20%, 25%, 50%, or 75% of the standard value corresponding to exudate, the pleural fluid is determined to be exudate. If the level of large particle lipids in the pleural fluid is within 5%, 10%, 15%, 20%, 25%, 50%, or 75% of the standard value corresponding to transudate, the pleural fluid is determined to be transudate. The standard value corresponding to exudate can be the average of the level of large particle lipids from two or more known exudates and the standard value corresponding to transudate can be the average of the level of large particle lipids from two or more known transudates. Similarly, if the level of indicator nanoparticles in the pleural fluid is within 5%, 10%, 15%, 20%, 25%, 50%, or 75% of the standard value corresponding to exudate, the pleural fluid is determined to be exudate. If the level of indicator nanoparticles in the pleural fluid is within 5%, 10%, 15%, 20%, 25%, 50%, or 75% of the standard value corresponding to transudate, the pleural fluid is determined to be transudate.

The control or standard values can be determined using the same method of determining the level of indicator nanoparticles, such as contrast agents and large lipids, as is used to determine the level of indicator nanoparticles, such as large lipids, in the pleural fluid. In preferred embodiments, the level of indicator nanoparticles, such as lipids, is determined by nuclear magnetic resonance (NMR), such as proton NMR ($^1$H-NMR). In some embodiments the method includes determining the level of large particle lipids by measuring the NMR signal corresponding to one or more of lipid signals selected from the group consisting of methyl protons (—CH$_3$), methylene protons ((—CH$_2$—)$_n$), and methene protons (—CH=CH—). For example, the lipid methyl protons (—CH$_3$) correspond to the signal at 0.84 ppm±0.15 on the NMR spectra, lipid methylene protons ((—CH$_2$—)$_n$) correspond to the signal at 1.26 ppm±0.15 on the NMR spectra, and lipid methene protons (—CH=CH—) correspond to the signal at 5.29 ppm±0.15 on the NMR spectra. In other preferred embodiments, the level of indicator nanoparticles, such as lipids, is determined by computed tomography (CT). For CT methods, use of contrast agents as the indicator nanoparticles is preferred.

Certain methods include an additional assay including but not limited to analysis by Light's criteria, or measuring: albumin gradient, NT-pro-BNP, BNP, C-reactive protein (CRP), cell counts of the pleural fluid, glucose concentration, pH value, adenosine deaminase (ADA) activity, amylase, cholesterol, triglyceride, cell-free DNA, protein zone electrophoresis, or any combination thereof. Additional assays or analysis are in addition to the measurement of large lipids.

In one embodiment the level of indicator nanoparticles, such as large lipids, in pleural fluid is carried out in vitro on a sample of pleural fluid obtained from the subject.

In other embodiments determining the level of indicator nanoparticles, such as large lipids, in pleural fluid is carried out in vivo using magnetic resonance spectroscopy (MRS). In still other embodiments determining the level of indicator nanoparticles, such as large lipids, in pleural fluid is carried out in vivo using computed tomography (CT). The pleural fluid can be classified as exudate or transudate with a sensitivity of 85%, 90%, 95%, 99%, or higher, a selectivity of 85%, 90%, 95%, 99%, or higher, or a combination thereof.

The disclosed methods can be coupled with a method of diagnosing the subject with a disease, disorder, or condition. For example, if the pleural fluid is determined to be transudate, the subject can be diagnosed with heart failure, cirrhosis, or nephrosis. If the pleural fluid is determined to be exudate, the subject can be diagnosed with pneumonia, malignancy, or thromboembolism.

The disclosed methods optionally include one or more additional diagnostic methods. The additional diagnostic method includes, but is not limited to cell counts in the pleural fluid; differential glucose or adenosine deaminase (ADA) analysis; cytologic analysis, bacterial cultures, pH measurement, or combinations thereof of the pleural fluid, or bronchoscopy, closed-needle biopsy of the pleura for histologic examination, thoracoscopy, helical CT, positron emission tomography (PET), or any combination thereof. The method optionally includes treating the subject for the presence of the pleural fluid or the disease or disorder diagnosed.

DETAILED DESCRIPTION OF THE INVENTION

I. Definitions

The terms "individual", "host", "subject", and "patient" are used interchangeably herein, and refer to a mammal, including, but not limited to, humans, rodents such as mice and rats, and other laboratory animals.

The term "biomarker" refers to an organic molecule produced by an organism that is indicative or correlative of a disease state. Biomarkers include, but are not limited to protein, lipids, metabolites, post-translationally modified proteins, etc.

The term "classify" refers to assigning a thing to a particular class or category. For example, a subject can be classified as exudate or transudate.

The term "sensitivity," as used in the context of classification and diagnosis, refer to the proportion of actual positives which are correctly identified as such (e.g. the percentage of sick people who are correctly identified as having the condition).

The terms "selectivity" and "specificity," as used in the context of classification and diagnosis, refer to the proportion of negatives which are correctly identified as such (e.g. the percentage of healthy people who are correctly identified as not having the condition).

The terms "large lipids," "large particle lipids," and "large lipid particles" refer to very low density lipoproteins (VLDL), low density lipoproteins (LDL), and high density lipoproteins (HDL).

The term "indicator nanoparticles" refer to nanoparticles that can be detected in samples in vitro or in situ in vivo. Useful indicator nanoparticles include nanoparticles 8-100 nm in mean diameter. Preferred indicator nanoparticles include nanoparticles 8-70 nm in mean diameter. More preferred indicator nanoparticles include nanoparticles 8-30 nm in mean diameter. Preferred indicator nanoparticles include large particle lipids and contrast agents. Preferred contrast agents include micelles and liposomes such as those described in Cormode et al., *Contrast Media Mol. Imaging* 9:37-52 (2014).

The terms "corresponds" and "corresponding to" refer to things that have a direct relationship to something else. For example, a standard or threshold value that corresponds to exudate pleural fluid is a value that is found in or is related to the value found in exudate pleural fluid. An NMR signal that corresponds to a lipid signal is an NMR signal that matches or is similar to an NMR signal generated by the indicated lipid.

II. Methods of Classifying Pleural Fluid

Some infections and diseases cause fluid to accumulate in the space between the lung and the rib cage or between the lung and the diaphragm. This collection of fluid is called a pleural effusion. Pleural effusion can be classified as exudative (high protein) or transudative (low protein). Generally, the level of lipids is also higher in exudative pleural fluid compared to transudative pleural fluid. It has been discovered that quantification of the lipid levels in pleural fluid can used to classify the fluid as exudate or transudate with a high degree of specificity and sensitivity. Further, it has also been discovered that exudative pleural effusion results from large pore size in the pleura. Based on this, it was also discovered that nanoparticles of suitable size can be used to indicate the classification of pleural effusion. As discussed in more detail below, classification of pleural fluid as exudate or transudate according to the disclosed methods can be used to improve disease diagnosis and treatment protocols.

The disclosed methods include determining the levels of indicator nanoparticles, such as lipids, in pleural fluid. More specifically, the methods include determining the levels of indicator nanoparticles, such as lipids, with certain particle sizes. Determining the level of indicator nanoparticles, such as lipids, in the pleural fluid can include determining an estimated, precise absolute value, or a relative value forindicator nanoparticles of certain particles sizes and comparing them to a standard. The levels of indicator nanoparticles, such as lipids, can be measured in vivo, or the levels of indicator nanoparticles, such as lipids, can be measured in vitro using a pleural fluid sample obtained from the subject. Once determined, the levels of indicator nanoparticles, such as lipids, are typically compared to a control to determine if the fluid is exudate or transudate. Generally, the levels of lipids, particularly lipids with large particles sizes, are higher in exudative pleural fluid than in transudative pleural fluid. This observation can also be used to compare levels of indicator nanoparticles of sizes similar to lipid particles to control levels of large particle lipids measured in controls.

A. Measuring the Lipid Content of Pleural Fluid

In one embodiment the lipid levels in pleural fluid are measured using proton nuclear magnetic resonance ($^1$H-NMR) spectroscopy. NMR is based on the principle that nuclei in a magnetic field absorb and re-emit electromagnetic radiation, and a wide range of techniques for quantifying various biomolecules in biological fluids have been developed. See, for example, Cheung, et al., *Acad. Radial.*, 18:377-383 (2011), Petersen, et al., *Clinical Chemistry*, 51(8):1457-1461 (2005), Otvos, et al., *Clinical Chemistry*, 38(9):1632-1638 (1992), and Otvos, et al., *Clinical Chemistry*, 37(3):377-386 (1991), which describe methods and techniques for quantifying and profiling lipids and lipoproteins in fluid samples using NMR.

The Example below shows that lipid profiling by $^1$H-NMR can be used to classify the fluid as exudate or transudate. The lipid signals generated by NMR analysis correspond to saturated and unsaturated lipids of different particle sizes. In the Example below, lipid signal integrals of lipid methyl protons (—CH$_3$; 0.84 ppm, also referred to herein as lipid 1), methylene protons ((—CH$_2$—)$_n$; 1.26 ppm, also referred to herein as lipid 2), and methene protons (—CH=CH—; 5.29 ppm, also referred to herein as lipid 3), which were consistent with lipid signal patterns reported previously (see Otvos, et al., *Clin. Chem.*, 37(3): 377-386 (1991) (Petersen, et al., *Clin. Chem.*, 51(8): 1457-1461 (2005), and Cheung, et al., *Acad. Radial.*, 18:377-383 (2011).

Lipids signals were analyzed using t-test and all show a statistically significant difference (p-values<0.0001) between the exudate and transudate. These data show that the lipid signals from the lipid molecules in PF can be determined using $^1$H-NMR spectroscopy, and their relative signals can be used to classify PF as exudate or transudate.

The disclosed methods can include measuring one or more lipid signal integrals or patterns using NMR. For example, the method can include measuring the signal integral or pattern of lipid methyl protons (—CH$_3$), methylene protons ((—CH$_2$—)$_n$), and methene protons (—CH=CH—), or combinations thereof. Lipid methyl protons (—CH$_3$) are generally found on NMR spectra at about 0.84 ppm±up to about 0.15. Lipid methylene protons ((—CH$_2$—)$_n$) are generally found on NMR spectra at about 1.26 ppm±up to about 0.15. Lipid methene protons (—CH=CH—) are generally found on NMR spectra at about 5.29 ppm±up to about 0.15.

Figure 4A:
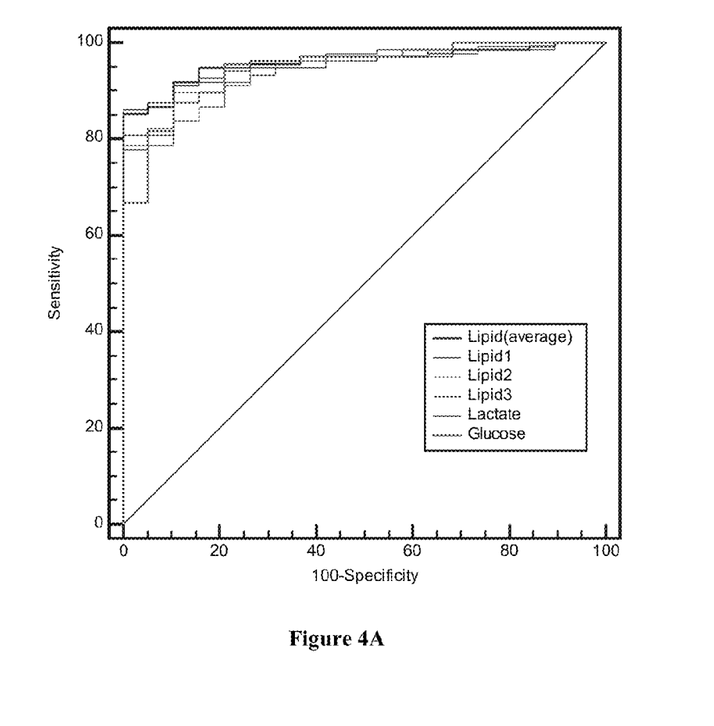
FIGS. 4A and 4B are area under the receiver operating characteristics (ROC) curves for lipid 1, 2, 3, lipid average, lactate, and glucose (4A) or lipid 1 and lipid 2 only (4B) to differentiate exudative from transudative NMR spectra of pleural effusions.
Figure 4B:
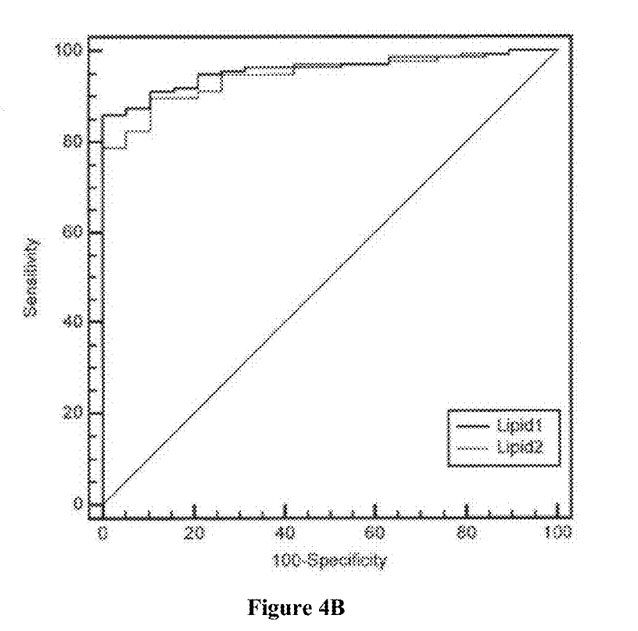
Figure 5:
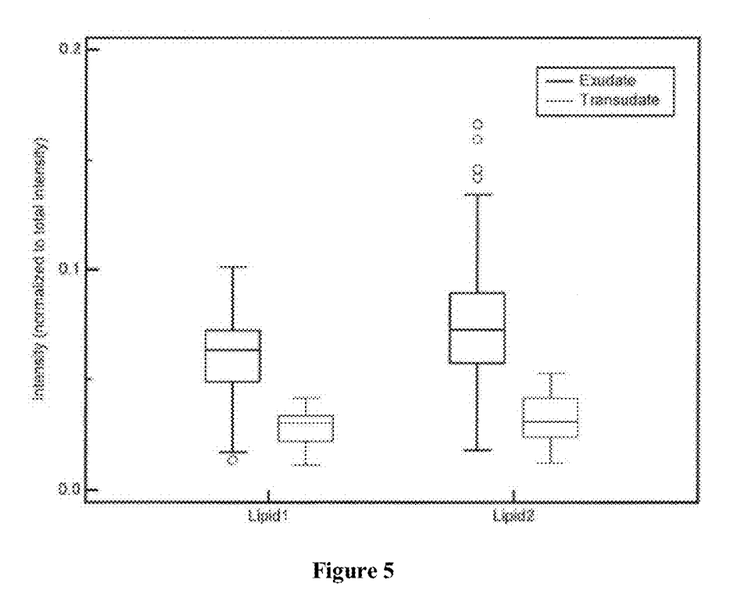
FIG. 5 is a Box-whisker plot of lipid 1 and lipid 2 NMR spectra signals to differentiate exudative from transudative NMR spectra of pleural effusions.

The Example below shows that the area-under-curve (AUC) of lipid methyl protons (—CH$_3$), methylene protons ((—CH$_2$—)$_n$), and methene protons (—CH=CH—) are 0.958 (95% confidence interval (CI): 0.913-0.984), 0.946 (95% CI: 0.898-0.976) and 0.946 (95% CI: 0.898-0.976) respectively (FIGS. 4A-4B and FIG. 5). Taking the mean of the three lipid signals together, i.e., lipid (average), it shows an AUC of 0.960 (95% CI=0.916-0.976) (FIG. 4A). The Example shows that using the optimal cutoffs, lipid methyl protons (—CH$_3$), methylene protons ((—CH$_2$—)$_n$), methene protons (—CH=CH—), and lipid (average) give sensitivities of 86.0% (95% CI=79.0%-91.4%), 89.7% (95% CI=83.3%-94.3%), 91.2% (95% CI=85.1%-95.4%) and 85.3% (95% CI=78.2%-90.8%), and specificities of 100% (95% CI=82.4%-100%), 89.5% (95% CI=66.9%-98.7%), 89.5% (95% CI=66.9%-98.7%) and 100% (95% CI=82.4%-100%) respectively.

Therefore, by measuring lipid methyl protons (—CH$_3$), the methylene protons ((—CH$_2$—)$_n$), methene protons (—CH=CH—), or a combination thereof by NMR, the pleural fluid can be determined to be exudate and transudate with a sensitivity of 80, 81, 82, 83, 84, 85, 86, 87, 88, 89, 90, 91, 92, 93, 94, 95, 96, 97, 98, 99, or 100% and a specificity of 80, 81, 82, 83, 84, 85, 86, 87, 88, 89, 90, 91, 92, 93, 94, 95, 96, 97, 98, 99, or 100%. For example, in some embodiments the pleural fluid can be determined to be exudate and transudate with a sensitivity of at least 86.0% and a specificity of 100% by measuring lipid methyl protons (—CH$_3$). In some embodiments the pleural fluid can be determined to be exudate and transudate with a sensitivity of at least 89.7% and a specificity of 89.5% by measuring lipid methylene protons ((—CH$_2$—)$_n$). In some embodiments the pleural fluid can be determined to be exudate and transudate with a sensitivity of at least 91.2% and a specificity of 89.5% by measuring lipid methene protons (—CH=CH—). In some embodiments the pleural fluid can be determined to be exudate and transudate with a sensitivity of at least 85.3% and a specificity of 100% by measuring lipid methyl protons, the methylene protons, and methene protons.

The lipid profiling can also include measuring of other lipid protons. For example, the method can include measuring allylic protons (—CH2-C=C—CH2-; 2.0 ppm), diallylic protons (=C—CH2-C=; 2.8 ppm), and protons from choline-containing compounds (CCC; 3.2 ppm). As with methyl protons, the methylene protons, and NMR spectral signals for methene protons, allylic protons, diallylic protons, and protons from choline-containing compounds are believed to be the same or higher in exudative pleural fluid than in transudative pleural fluid. In some embodiments, measuring additional levels of additional lipid such as methene protons, allylic protons, diallylic protons, protons from choline-containing compounds or combinations thereof further enhance the specificity or sensitivity of the assay.

The above techniques can be used to measure lipids from large particle lipids and introduced indicator nanoparticles that contain lipid, such as micelles and liposomes. Indicator nanoparticles can also include labels or be otherwise detectable. For example, indicator nanoparticles can be contrast agents. Contrast agents generally are detectable in vivo using noninvasive imaging techniques such as computed tomography.

Use of indicator nanoparticles other than naturally present lipid particles generally requires introduction of the indicator nanoparticles. Generally, indicator nanoparticles can be introduced intravenously and can be introduced at a time sufficiently in advance of detection or sample acquisition to allow the indicator nanoparticles to reach the pleura and to pass through (if such passage is possible in the subject). Numerous techniques for introducing labeled or detectable components and methods for their detection are known and can be adapted for use with the disclosed methods and indicator nanoparticles.

1. In Vitro Techniques

The methods of classifying pleural fluid can be carried out in vitro on a sample obtained from a subject. Methods of obtaining pleural fluid from a subject are known in the art. A collection of pleural fluid that accumulates in the space between the lung and the rib cage or between the lung and the diaphragm is referred to as a pleural effusion. Pleural effusions can be detected, for example, on a chest x-ray. A sample of fluid can be retrieved with a needle in a procedure known as thoracentesis. For example, a typical procedure may include inserting a needle on an empty syringe through the chest wall into the pleural fluid pocket. Usually this pocket is around one inch below the skin surface and can be accessed from the subjects back.

Preparation of the fluid sample for lipid profiling is known in the art. An exemplary method of preparing a sample for NMR is provided in the Example below. Samples can be collected or transferred into sterile containers. The samples can be centrifuged to obtain a clear supernatant for testing. An exemplary centrifugation step is 3000 rpm for 10 minutes at 4° C. The sample can be stored frozen, for example at −20° C., −80° C., or −120° C. At the time of analysis, the sample is mixed with a buffer suitable for NMR analysis. An exemplary buffer is 1.5 M $KH_2PO_4$ in 100% $D_2O$ containing 0.1% trimethylsilyl propanoic acid (TMSP). An exemplary mixing of sample and buffer is a ratio of 4 parts sample to 1 part buffer (i.e., 480 μL of sample and 120 μL of buffer solution). NMR can be carried out with small volume samples. An exemplary NMR sample is about 550 μL including both sample and buffer.

NMR provides a number of advantages over alternative methods of measuring lipids. As discussed above, samples suitable for NMR can be prepared by mixing the pleural fluid directly with buffer, and typically do not require any chemical reactions. NMR instrumentation can be equipped with an automated sample delivery system in which multiple samples can be analyzed in parallel.

In some embodiments, however, one of more other in vitro techniques for measuring lipids is used in addition to, or as an alternative to, NMR. Other techniques for quantifying or profiling lipids in biological sample are known in the art. The methods include physical separation techniques such as gradient gel electrophoresis, ultracentrifugation, and chromatography. Physical separation techniques methods can be costly and time consuming Less expensive, but also somewhat less accurate, methods include selective precipitation. Methods for sample preparation and use of these techniques to quantitate and profile lipid and lipoproteins are known in the art.

2. In Vivo Techniques

The methods of classifying pleural fluid can also be carried out in vivo. In a preferred embodiment, lipid levels in pleural fluid are determined using in vivo magnetic resonance spectroscopy (MRS). Magnetic Resonance Spectroscopy (MRS) is an analytical technique that has been used to complement the more common Magnetic Resonance Imaging (MRI) in the characterization of tissue. Both techniques use signals from hydrogen protons ($^1H$), but MRI uses the information to create 2-dimensional images of the tissue, while MRS uses $^1H$ signals to determine the relative concentrations of target metabolites. MRS is used, for example, to measure metabolic changes in tumors and in the brain under neurodegenerative conditions. See, for example, Glunde, et al., *NMR Biomed.*, 24(6): 673-690 (2011). The techniques used in the areas of tumor and brain monitoring can be adapted to analyzing pleural fluid in subjects in vivo, and lipid levels in the fluid can be determined using the lipid spectral peaks discussed above.

B. Determining the Pleural Fluid Classification

Once the level of indicator nanoparticles, such as lipids, is measured, the classification of pleural fluid is determined. Absolute or relative data values are compared to a standard or control to determine if the fluid is exudative and transudative.

1. Data Analysis a. Absolute Quantitation

As discussed in Cheung, et al., *Acad. Radial.*, 18:377-383 (2011), Petersen, et al., *Clinical Chemistry*, 51(8):1457-1461 (2005), Otvos, et al., *Clinical Chemistry*, 38(9):1632-1638 (1992), and Otvos, et al., *Clinical Chemistry*, 37(3):377-386 (1991), NMR can be used to profile and quantitate absolute values of lipids and lipoproteins. The absolute values determined using NMR are generally found to correlate well with the values measured using other methods of measurement including ultracentrifugation. Therefore, in some embodiments, the level of lipids in pleural fluid is measured as an estimated or precise absolute quantitative value corresponding to the actual level of the lipids in the fluid sample.

Absolute quantification (AQ), also referred to as absolute quantitation) implies that concentrations are expressed in biochemical units. The corresponding with metabolites in the pleural fluid sample have certain resonance frequencies, line widths (full width at half maximum of the peak's height), line shapes (e.g., lorentzian or Gaussian), phases, and areas. The peaks are separated owing to differences in resonance frequency, which are caused by the difference in the chemical environment of the different nuclei. The molecular structure of lipids in pleural fluid is reflected by the characteristic peak pattern of the lipids discussed above. The area of a peak is directly proportional to the number of nuclei that contribute to it and to the concentration of the metabolite to which the nuclei belong. However, the peak areas are also influenced by other factors, including T1 and T2 relaxation times.

Generally, for absolute quantification, accurate peak areas for the relevant metabolites are determined and careful calibration is used to convert peak areas to metabolite concentrations to which the metabolite signals are referenced.

b. Relative Quantitation

Indicator nanoparticle concentrations (such as lipid concentrations) can also be presented qualitatively as ratios (e.g., relative to a standard such as another metabolite in the sample) rather than as absolute concentrations (also referred to as relative quantification). One of the simplest approaches is the internal endogenous marker method. With this approach, one of the measured peaks, originating from an endogenous metabolite, serves as a concentration standard. Peak ratios (possibly corrected for factors such as relaxation) are converted into concentrations by using a value for the reference metabolite, whose concentration is invariant in exudative and transudative fluids.

Data analysis for absolute and relative data quantitation can include a number of techniques which are known in the art and include, for example, integration and peak fitting. See, for example, Jansen, et al., *Radiology*, 240:318-332 (2006), which provides methods and techniques for system calibration and data analysis that can be used for absolute and relative quantification of NMR data in vitro and in vivo.

2. Comparison to a Control

Once the data is quantified, it is compared to a control or standard to determine if the fluid is exudative and transudative. The control can be an absolute value or range of absolute values. The control can be a relative value or range of relative values. For example, the control value or range of values for exudative fluid can be determined by measuring the levels of lipids in one or more samples known to be exudative fluid. Likewise, the control value or range of values for transudative fluid can be determined by measuring the levels of lipids in one or more samples known to be transudative fluid. Introduced or artificial indicator nanoparticles can be compared, for example, to true controls (levels of the indicator nanoparticle observed in unaffected subjects) or to comparative controls such as the lipid levels in unaffected subjects.

One of skill in the art will understand how to prepare or select an appropriate control based on the nature of the test sample. For example, if the value for the test sample is based a lipid 1 profile, the control values or ranges of values can be based on a lipid 1 profile of control samples known to be exudative fluid and transudative fluid. Likewise, if the value for the test sample is based lipid 1, 2, and 3 profiles, the control values or ranges of values can be based on lipid 1, 2, and 3 profiles of control samples known to be exudative fluid and transudative fluid.

The values or range of values for controls can be determined using any suitable method known in the art, including those discussed herein such as electrophoresis, ultracentrifugation, and NMR. The control values can be determined in vitro or in vivo, for example, using in vivo MRS. In a preferred embodiment, the values for the control samples are determined in the same manner or using the techniques and protocols as is used to determine the value(s) of the test sample.

In some embodiments, the test fluid is determined to be exudative fluid if the test value is within 5%, 10%, 15%, 20%, 25%, 50%, or 75% of a control exudative fluid. In some embodiments, the test fluid is determined to be transudative fluid if the test value is within 5%, 10%, 15%, 20%, 25%, 50%, or 75% of a control transudative fluid.

In some embodiments, the control is a single threshold value or range of values. For example, in some embodiments the test fluid is determined to exudative if the test value is above a threshold value and the test fluid is determined to be transudative fluid if the test value is below a threshold value. In some embodiments, the test fluid is determined to exudative if the test value is 5%, 10%, 15%, 20%, 25%, 50%, or 75% above a threshold value and the test fluid is determined to be transudative fluid if the test value is 5%, 10%, 15%, 20%, 25%, 50%, or 75% below a threshold value. In some embodiments, the threshold value is the average of a control exudative fluid and a control transudative fluid. A threshold value is a value that is used as a threshold for a comparison, such as for classifying values as above or below the threshold value. A standard or standard value is a value that is used as a standard for a comparison, such as for classifying values as above or below the standard value. A control or control value is a value that is used as a control for a comparison, such as for classifying values as above or below the control value.

In some embodiments, a test fluid is determined to be transudative fluid by being determined not be exudative fluid. In some embodiments, a test fluid is determined to be exudative fluid by being determined not be transudative fluid.

C. Combination Methods

In some embodiments, the methods of disclosed methods of classification are combined with other methods of classifying pleural fluid. For example, in some embodiments, the methods include measuring one or more additional biomarkers of used to classify pleural fluid. The biomarkers are in addition to the large lipids that are measured. The test sample is selected as exudative fluid or transudative fluid if it is determined to be exudative or transudative using the methods disclosed herein and by measuring at least one other biomarker according to a method that is known in the art. Example biomarkers include, but are not limited to, Light's critera, albumin gradient, NT-pro-BNP, BNP (Valdes, et al., *Arch Bronconeumol.*, 47(5):246-51 (2011), C-reactive protein (CRP) (Porcel, et al., *Eur. J. Intern. Med.*, 23(5):447-50 (2012)), cell counts (both red blood cells and white blood cells), glucose concentration, pH value, adenosine deaminase (ADA) activity (Chen, et al, *Clin Chim Acta.*, 341(1-2):101-7 (2004), amylase, cholesterol (Vaz, et al., *Curr Opin Pulm Med.*, 7(4):183-6 (2001), Valdes, et al., *Transl. Res.*, 155(4):178-84)), triglyceride (Valdes, et al, *Lung*, 188(6):483-9 (2010)), cell-free DNA (Chan, et al., *Clin Chem.*, 49(5):740-5 (2003)), protein zone electrophoresis (Chen and Lam, *Clin Chem.*, 45(10):1882-5 (1999)) among others. Criteria and values used for classifying fluid as exudative pleural fluid according to known methods are known in the art. See, for example, Table 1 below, reproduced from Porcel, *Respirology*, 16:44-52 (2011).

TABLE 1

Measures of diagnostic accuracy for tests that identify an exudative pleural effusion[†]

| | N | Sensitivity, % (95% CI) | Specificity, % (95% CI) | LR+ | LR− |
|---|---|---|---|---|---|
| PF protein >3 g/dL | 2283 | 86.4 (84.7-88) | 83.2 (79.8-86) | 5.14 (4.26-6.2) | 0.16 (0.14-0.19) |
| PF/S protein >0.5 | 2027 | 86.2 (84.4-88) | 88.3 (85.2-90.8) | 7.35 (5.78-9.35) | 0.16 (0.14-0.18) |
| PF LDH LP >312 U/L[‡] | 2260 | 78 (76-80) | 95.2 (93-96.7) | 16.22 (11.14-23.62) | 0.23 (0.21-0.25) |
| PF/S LDH >0.6 | 1714 | 90.1 (88.4-91.6) | 83.1 (79.2-86.4) | 5.33 (4.31-6.59) | 0.12 (0.10-0.14) |
| Cholesterol >45 mg/dL | 517 | 87.2 (83.3-90.3) | 83.2 (77-88) | 5.20 (3.72-7.27) | 0.15 (0.12-0.20) |
| S-PF albumin ≤1.2 g/dL | 209 | 51.3 (40.3-62.2) | 94.7 (89.5-97.4) | 9.75 (4.59-20.71) | 0.51 (0.41-0.65) |
| S-PF protein ≤3.1 g/dL | 2027 | 85 (83.2-86.7) | 84.3 (81-87.2) | 5.42 (4.42-6.64) | 0.18 (0.16-0.20) |
| PF protein or PF LDH | 2277 | 95.1 (94-96) | 80.4 (76.8-83.5) | 4.85 (4.09-5.76) | 0.06 (0.05-0.08) |
| PF/S protein or PF LDH | 2207 | 95 (94-96) | 84.7 (81.4-87.6) | 6.24 (5.08-7.66) | 0.06 (0.05-0.07) |
| Light's criteria | 2115 | 97.5 (96.7-98.2) | 73.8 (69.4-77.7) | 3.72 (3.17-4.36) | 0.03 (0.02-0.05) |

[†]This is an unpublished update from our database.
[‡]This figure represents more than two-thirds the upper limits of our laboratory's normal serum LDH.
CI, confidence interval; LR, likelihood ratio; PF, pleural fluid; PF/S, pleural fluid to serum ratio; S-PF, gradient between the serum and the pleural fluid.

III. Methods of Using Classified Pleural Fluid

Classifying pleural fluid as exudative fluid or transudative fluid can be used to narrow down the underlying causes of certain diseases, disorders, and conditions. Therefore, the methods of classifying pleural fluid can be integrated into diagnostic protocols, treatment regimes, or a combination thereof.

A. Diagnosis of Disease

The methods of pleural fluid classification disclosed herein can be used alone or in combination with other diagnostic methods to diagnose a subject with a disease or condition.

1. Transudates

Transudates can result from imbalances in hydrostatic and oncotic forces. They can be caused by clinical conditions such as heart failure, cirrhosis, nephrotic syndrome, atelectasis, peritoneal dialysis, constrictive pericarditis, superior vena caval obstruction, and urinothorax. Therefore, in some embodiments, subject with transudative fluid is diagnosed with heart failure, cirrhosis, nephrotic syndrome, atelectasis, peritoneal dialysis, constrictive pericarditis, superior vena caval obstruction, or urinothorax.

In preferred embodiments, the method of diagnosing a subject with a disease, condition, or disorder includes classification of the pleural fluid as transudative and identification of one or more clinical symptoms typically associated with the disease. In most cases transudative fluid is associated with heart failure, cirrhosis, or nephrosis. Therefore, in preferred embodiment, the method includes determining if the subject has one or more additional symptoms of heart failure, cirrhosis, or nephrosis and diagnosing he/she accordingly. The symptoms are in addition to the classification of the pleural fluid.

2. Exudates

Exudates can occur when the local factors influencing the accumulation of pleural fluid are altered. Pneumonia, malignancy, and thromboembolism account for most exudative effusions in the United States.

Additional tests that can performed if the test fluid is determined to be exudates are discussed in Porcel, et al., Am. Fam. Physician, 1; 73(7):1211-1220 (2006) and include, but are not limited to, cell counts and differential, glucose, adenosine deaminase (ADA), and cytologic analysis. Bacterial cultures and pH should be tested if infection is a concern.

The predominant WBC population is determined by the mechanism of pleural injury and the timing of the thoracentesis in relation to the onset of the injury. Thus, the finding of neutrophilrich fluid heightens suspicion for parapneumonic pleural effusion (an acute process), whereas a lymphocyte-predominant fluid profile suggests cancer or tuberculosis (a chronic process).

A low pleural fluid pH value has prognostic and therapeutic implications for patients with parapneumonic and malignant pleural effusions. A pH value less than 7.20 in a patient with a parapneumonic effusion indicates the need to drain the fluid. In a patient with malignant pleural effusion, a pleural fluid pH value less than 7.30 is associated with a shorter survival and poorer response to chemical pleurodesis. When a pleural fluid pH value is not available, a pleural fluid glucose concentration less than 60 mg per dL can be used to identify complicated parapneumonic effusions.

ADA is an enzyme that plays an important role in lymphoid cell differentiation. A pleural fluid ADA level greater than 40 U per L (667 nkat per L) has a sensitivity of 90 to 100 percent and a specificity of 85 to 95 percent for the diagnosis of tuberculous pleurisy. The specificity rises above 95 percent if only lymphocytic exudates are considered. In areas where the prevalence of tuberculosis is low, the positive predictive value of pleural ADA declines but the negative predictive value remains high.

Cultures for both aerobic and anaerobic bacteria will identify the responsible microorganism in about 40 percent of parapneumonic effusions (70 percent if fluid is grossly purulent).

Cytology is positive in approximately 60 percent of malignant pleural effusions. Negative test results are related to factors such as the type of tumor (e.g., commonly negative with mesothelioma, sarcoma, and lymphoma); the tumor burden in the pleural space; and the expertise of the cytologist. The diagnostic yield may be somewhat improved by additional pleural taps.

B. Other Diagnostic Procedures

In some embodiments, the methods of classifying pleural fluid disclosed herein are combined with additional diagnostic procedures, such as those discussed in Porcel, et al., Am. Fam. Physician, 1; 73(7):1211-1220 (2006). For example, Helical CT can be used to diagnose deep venous thrombosis when combined with CT venography of the pelvis and lower extremities, and can distinguish malignant from benign pleural disease. CT findings indicative of malignant disease are the presence of pleural nodules or nodular pleural thickening, circumferential or mediastinal pleural thickening, or infiltration of the chest wall or diaphragm. Positron emission tomography (PET) has also been used to distinguish between benign and malignant pleural diseases. Additional diagnostic methods are in addition to the classification of the pleural fluid.

Bronchoscopy is useful whenever an endobronchial malignancy is likely, as suggested by one or more of the following characteristics: a pulmonary infiltrate or a mass on the chest radiograph or CT scan, hemoptysis, a massive pleural effusion, or shift of the mediastinum toward the side of the effusion.

Closed-needle biopsy of the pleura for histologic examination classically has been recommended for undiagnosed exudative effusions when tuberculosis or malignancy is suspected. The combination of histology (80 percent sensitivity) and culture (56 percent sensitivity) of pleural biopsy tissue establishes the diagnosis of tuberculosis in up to 90 percent of patients. This diagnosis is also strongly suggested by a high ADA level in the pleural fluid as discussed above.

Cytology is superior to blind pleural biopsy for the diagnosis of pleural malignancy. The diagnostic yield from pleural biopsy is typically higher when it is used with some form of image guidance to identify areas of particular thickening or nodularity.

Thoracoscopy is diagnostic in more than 90 percent of patients with pleural malignancy and negative cytology. Therefore, it is a preferred diagnostic procedure in patients with cytology-negative pleural effusion who are suspected of having pleural malignancy. Thoracoscopy also offers the possibility of effective pleurodesis during the procedure.

C. Methods of Treatment

In some embodiments, the methods of classification and diagnosis disclosed herein are coupled to a method of treatment. Transudative effusions usually respond to treatment of the underlying condition (e.g., diuretic therapy). In some methods, the pleural fluid is classified as either transudate or exudate, the subject is diagnosed with an underlying condition, and the subject is treated using compositions or methods that known in the art for treating the underlying condition.

IV. Systems for Classifying Pleural Fluids

Systems for classifying pleural fluids are also provided. The systems can process a sample from a subject and analyze the sample for levels of one or more of the lipids disclosed herein, and apply one or more of the rules described herein. Typically, the system includes a means for detecting or quantifying the lipid, a computer, and an output means for reporting whether or not the subject has transudate or exudate. The system can also be used for assessing the efficacy of a treatment for pleural fluid. For example, one embodiment provides a method having the steps of administering a drug to a subject having pleural fluid, and determining if the pleural fluid is decreased (indicating the drug if efficacious), or if the pleural fluid remains the same or is increase (indicating the drug is not efficacious).

Another embodiment provides a computer-implemented method of selecting a subject for treatment by inputting into a computer the concentration test values determined according to the disclosed method reporting if the pleural fluid is transudate or exudate by comparing the test value to a control as discussed herein.

The test data can be obtained by NMR. The method can be used to assist in the diagnosis of diseases associated with pleural fluid accumulation. An exemplary system is the Laboratory Information System.

EXAMPLE

Pleural Effusion NMR Signals from Lipid Particles are Biomarkers of Exudative Pleural Effusions Materials and Methods Sample Preparations The samples were collected into sterile plain bottle followed by centrifugation for 10 minutes with 3000 rpm at 4° C. to obtain a clear supernatant. At the time of analysis, 480 µL of sample was mixed with 120 µL of buffer solution (1.5 M $KH_2PO_4$ in 100% $D_2O$ containing 0.1% trimethylsilyl propanoic acid (TMSP)). Sample was mixed and 550 µL of each was transferred to a 5 mm NMR tube freshly for NMR analysis.

NMR Experiments

All NMR spectra were acquired on a Bruker Avance 600 MHz NMR spectrometer (Bruker Biospin, Rheinstetten, Germany) at 298K. Samples were automatically loaded via SampleXpress. Water resonance was suppressed with pre-saturation during a relaxation delay of 4 s. Data for Bruker 'cpmgprld' pulse programs (i.e., relaxation edited Carr-Purcell-Meiboom-Gill (CPMG) pulse sequence) was applied to enhance the detection of small molecular weight compound. The acquisition records with 64 scans, covering spectral width of 12019.230 Hz into 32 k data points. Phase and baseline were corrected automatically and referenced to the internal standard TSP (0.000 ppm) using TopSpin (version 3.1, Bruker BioSpin, Rheinstetten, Germany). All spectra were reduced to data using Amix (version 3.9.11, Bruker BioSpin) and calibrated internally to the lactate peak of the C$\underline{H}_3$ signal at the chemical shift of 1.33 ppm. Assignment of the NMR spectra was matched to the BBIOREFCODE-2-0-0 database (Bruker Biospin, Rheinstetten, Germany), Human Metabolome Database (Version 3.0) (Wishart, et al., Nucleic Acids Res 41(Database issue): D801-807 (2013)) Chenomx NMR suite and literatures.

Data Processing and Statistical Analysis

The bucketing of the spectra was performed over the range of 0.5 to 10.0 ppm using advanced bucketing as the $^1$H-NMR Bucket method (AMIX). The subregion 4.45-4.90 ppm was removed to reduce the variability introduced from water signals. Data were normalized by the total signal intensity and filtered using SNV filtering (SIMCA-P13) (Umetrics, Umeå, Sweden). The data were analyzed using PCA and OPLS-DA using SIMCA-P13 software. Other statistical analysis was performed using MedCalc (Version 12.2.1.0).

Results

Pleural fluid was obtained from 155 patients. The PF samples were classified using the modified Light's criteria with a matching clinical diagnosis as reference standard. In brief, for the modified Light's criteria, PF was regarded as exudate if at least one of the following were present: ratio of pleural fluid protein to serum protein is greater than 0.5; ratio of pleural fluid lactate dehydrogenase (LDH), and serum LDH is greater than 0.6; or pleural fluid LDH is greater than 0.6 or two-third times the upper limit of normal in serum. Using this criteria, there were 136 exudative pleural effusion samples and 19 transudative pleural effusion samples. Using NMR spectroscopy, a significant increase in lipid signals, particularly lipids corresponding to $CH_3$ and $(CH_2)n$, were found in exudative pleural effusion.

Figure 1:
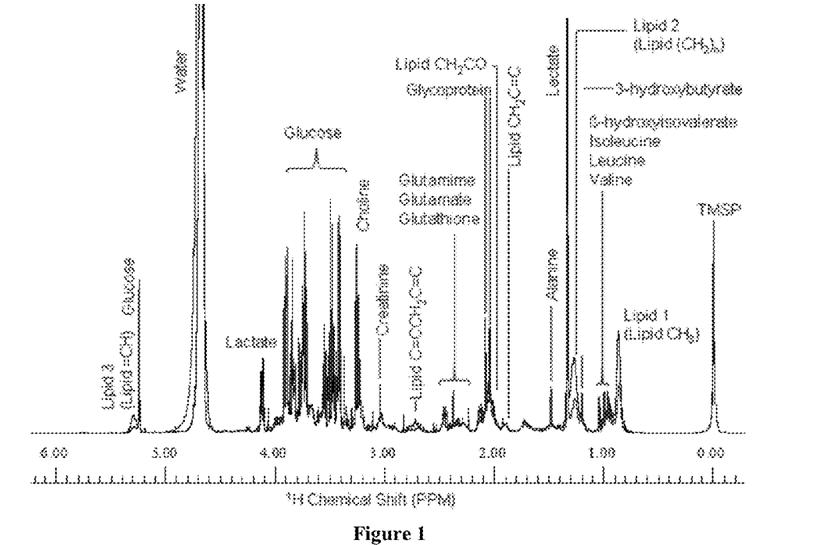
FIG. 1 is an overlay of representative 600 MHz $^1$H-Nuclear Magnetic Resonance ($^1$H-NMR) spectra of pleural fluid exudate and transudate obtained using a Carr-Purcell-Meiboom-Gill (CPMG) imaging sequence.
Figure 2A:
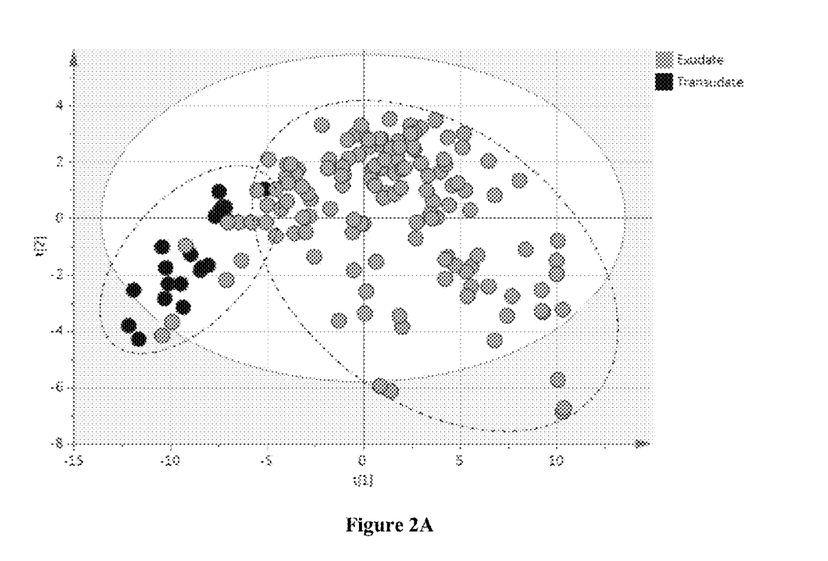
FIGS. 2A and 2B are the score plot (2A) and loading plot (2B) of a principal component analysis (PCA) of NMR spectra from pleural fluid exudates and transudates.
Figure 2B:
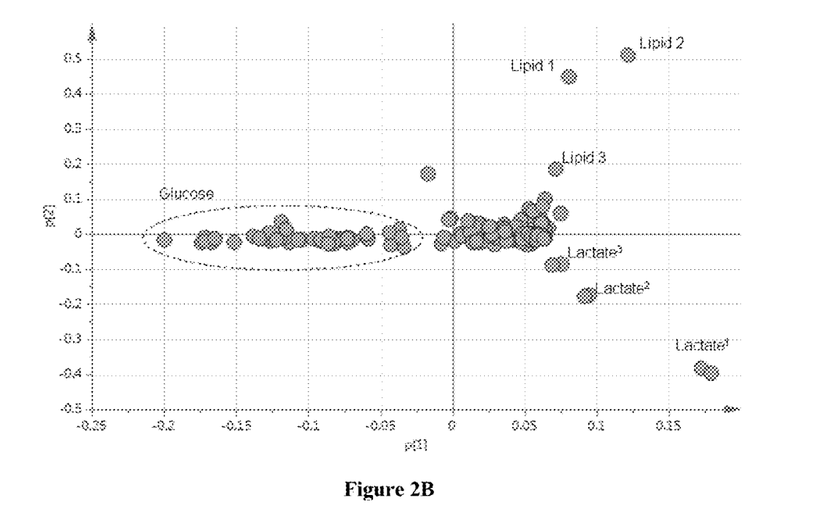
Figure 3A:
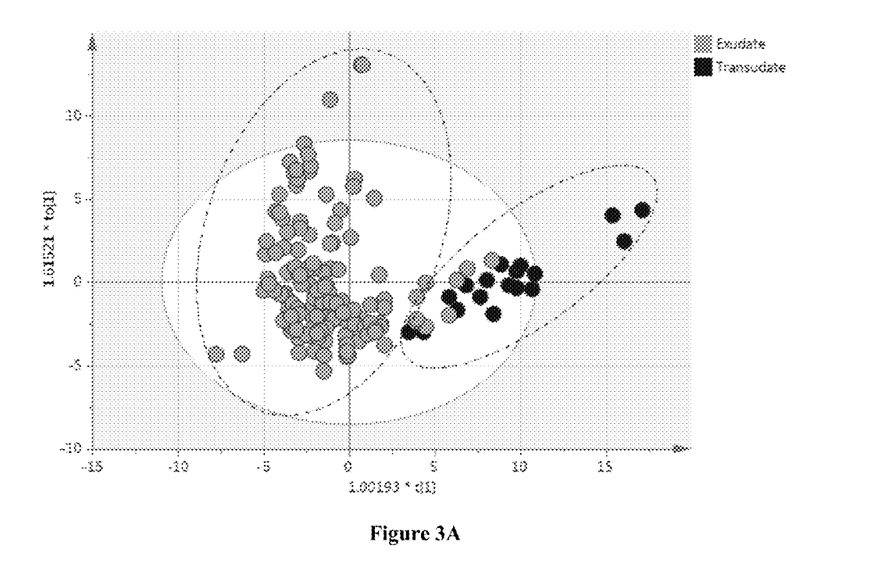
FIGS. 3A and 3B are the score plot (3A) and loading plot (3B) of a projection to latent structures discriminant analysis (PLS-DA) of NMR spectra from pleural fluid exudates and transudates.
Figure 3B:
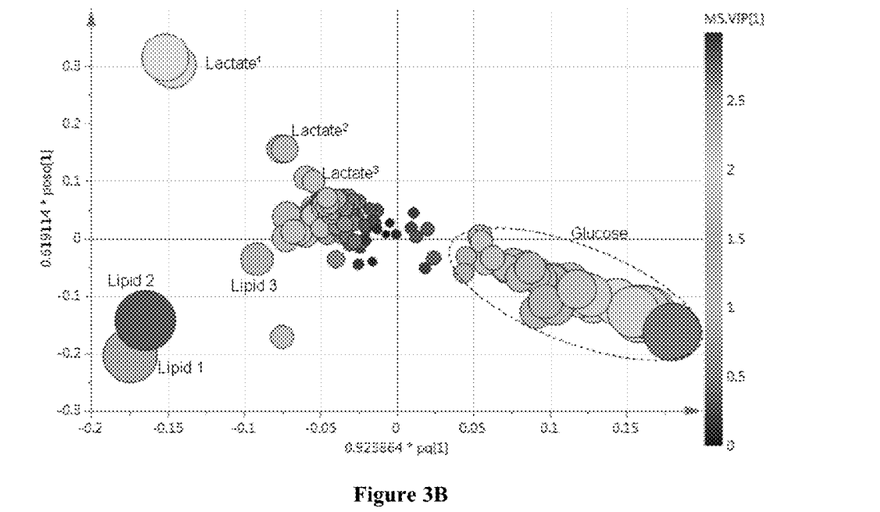

A representative CPMG NMR spectra of pleural effusion are shown in FIG. 1. Consistent with the biochemical nature of exudates NMR spectra from exudates showed more intense and complex signals than that of transudates. Score plots from PCA and OPLS-DA showed a clear clustering of exudative from transudative PF (FIGS. 2A-2B and FIGS. 3A-3B). From the loading plots, three distinctive lipid signals were observed at 0.84 ppm, 1.26 ppm and 5.29 ppm, labeled as lipid 1, lipid 2 and lipid 3, respectively. These patterns of lipid signals in PF resembled those seen in plasma using NMR spectroscopy (Otvos, et al., *Clin. Chem.*, 37(3): 377-386 (1991) (Petersen, et al., *Clin. Chem.*, 51(8): 1457-1461 (2005)). Lipid 1 signal at 0.84 ppm corresponds to C$\underline{H}_3$ of lipid, lipid 2 signal at 1.26 ppm corresponds to (C$\underline{H}_2$). of lipid and lipid 3 at 5.29 ppm corresponds to —CH=CH— of lipid.

The area-under-curve (AUC) of lipid 1, 2 and 3 are 0.958 (95% confidence interval (CI): 0.913-0.984), 0.946 (95% CI: 0.898-0.976) and 0.946 (95% CI: 0.898-0.976) respectively (FIGS. 4A-4B and FIG. 5). Taking the mean of the three lipid signals together, i.e., lipid (average), it shows an AUC of 0.960 (95% CI=0.916-0.976) (FIG. 4A). Using the optimal cutoffs, the lipid 1, 2, 3 and lipid (average) give sensitivities of 86.0% (95% CI=79.0%-91.4%), 89.7% (95% CI=83.3%-94.3%), 91.2% (95% CI=85.1%-95.4%) and 85.3% (95% CI=78.2%-90.8%), and specificities of 100% (95% CI=82.4%-100%), 89.5% (95% CI=66.9%-98.7%), 89.5% (95% CI=66.9%-98.7%) and 100% (95% CI=82.4%-100%) respectively. Lipids signals were analyzed using t-test and all show a statistically significant difference (p-values<0.0001) between the exudate and transudate.

The relatively high levels of lipid seen in exudative PF is believed to be the result of increasing permeability of capillary which allow the passage of large lipid particles to migrate into the pleural space and accumulated in pleural fluid from the plasma circulation. In contrast, in transudative pleural effusion, the capillary permeability remains intact and thus, migration of larger lipid particles through the capillaries and into the pleural space is limited or prevented. These data show that the lipid signals from the lipid molecules in PF can be determined using $^1$H-NMR spectroscopy, and their relative signals can be used to classify PF as exudate or transudate.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of classifying pleural fluid comprising determining the level of indicator nanoparticles in the pleural fluid of a subject, wherein pleural fluid with a higher level of indicator nanoparticles compared to a control is determined to be exudate and pleural fluid with a lower level of indicator nanoparticles compared to the control is determined to be transudate, wherein the control is a single average threshold value determined by averaging of the level of indicator nanoparticles from known exudates and transudates.

2. The method of claim 1 wherein the threshold value is determined using the same method of determining the level of indicator nanoparticles as is used to determine the level of indicator nanoparticles in the pleural fluid.

3. The method of claim 1 wherein the indicator nanoparticles comprise contrast agent nanoparticles or large particle lipids.

4. The method of claim 1 wherein the level of indicator nanoparticles is determined by nuclear magnetic resonance (NMR).

5. The method of claim 4 wherein the NMR is proton NMR ($^1$H-NMR).

6. The method of claim 5 wherein determining the level of indicator nanoparticles comprises measuring the NMR signal corresponding to one or more of lipid signals selected from the group consisting of methyl protons (—CH$_3$), methylene protons ((—CH$_2$—)$_n$), and methene protons (—CH=CH—).

7. The method of claim 6 wherein the lipid methyl protons (—CH$_3$) correspond to the signal at 0.84 ppm±0.15 on the NMR spectra, lipid methylene protons ((—CH$_2$—)$_n$) correspond to the signal at 1.26 ppm±0.15 on the NMR spectra, and lipid methene protons (—CH=CH—) correspond to the signal at 5.29 ppm±0.15 on the NMR spectra.

8. The method of claim 6 comprising measuring the NMR signal corresponding to two or more lipid signals selected from the group consisting of methyl protons (—CH$_3$), methylene protons ((—CH$_2$—)$_n$), and methene protons (—CH=CH—).

9. The method of claim 8 comprising measuring the NMR signal corresponding to methyl protons (—CH$_3$), methylene protons ((—CH$_2$—)$_n$), and methene protons (—CH=CH—).

10. The method of claim 1 wherein the level of indicator nanoparticles is determined by computed tomography (CT).

11. The method of claim 1 further comprising performing an additional assay or analysis of one or more additional biomarkers to classify the fluid as exudate or transudate.

12. The method of claim 11 wherein the additional assay or analysis of one or more additional biomarkers comprises analysis of Light's criteria, or measuring albumin gradient, NT-pro-BNP, BNP, C-reactive protein (CRP), cell counts, glucose concentration, pH value, adenosine deaminase (ADA) activity, amylase, cholesterol, triglyceride, cell-free DNA, protein zone electrophoresis, or any combination thereof.

13. The method of claim 1 wherein determining the level of indicator nanoparticles in pleural fluid is carried out in vitro on a sample of pleural fluid obtained from the subject.

14. The method of claim 1 wherein determining the level of indicator nanoparticles in pleural fluid is carried out in vivo using magnetic resonance spectroscopy (MRS).

15. The method of claim 1 wherein determining the level of indicator nanoparticles in pleural fluid is carried out in vivo using computed tomography (CT).

16. The method of claim 1 wherein the pleural fluid is determined to be exudate or transudate with a sensitivity of 85%, 90%, 95%, 99%, or higher.

17. The method of claim 1 wherein the pleural fluid is determined to be exudate or transudate with a selectivity of 85%, 90%, 95%, 99%, or higher.

18. The method of claim 1 wherein the pleural fluid is determined to be exudate or transudate with a sensitivity of 85%, 90%, 95%, 99%, or higher and a selectivity of 85%, 90%, 95%, 99%, or higher.

19. The method of claim 1 further comprising diagnosing the subject with a disease, disorder, or condition.

20. The method of claim 19 wherein if the pleural fluid is determined to be transudate, the subject is diagnosed with heart failure, cirrhosis, or nephrosis.

21. The method of claim 20 further comprising treating the subject.

22. The method of claim 21 wherein the treatment comprises diuretic therapy.

23. The method of claim 22 wherein the treatment further comprises treating the subject for heart failure, cirrhosis, or nephrosis.

24. The method of claim 23 further comprising performing one or more additional diagnostic methods.

25. The method of claim 24 wherein the additional diagnostic method includes cell counts, differential glucose or adenosine deaminase (ADA) analysis, cytologic analysis, bacterial cultures, pH measurement, or combinations thereof of the pleural fluid.

26. The method of claim 19 further comprising performing one or more additional diagnostic methods.

27. The method of claim 19 wherein if the pleural fluid is determined to be exudate, the subject is diagnosed with pneumonia, malignancy, or thromboembolism.

28. The method of claim 27 further comprising treating the subject.

29. The method of claim 19 further comprising performing bronchoscopy, closed-needle biopsy of the pleura for histologic examination, thoracoscopy, helical CT, positron emission tomography (PET), or a combination thereof.

30. A method of assisting in the diagnosis of a disease, disorder, or condition in a subject comprising classifying the pleural fluid of the subject as exudate or transudate according to the method of claim 1.

* * * * *